(12) United States Patent
DeYoung (10) Patent No.: US 7,000,251 B2
(45) Date of Patent: Feb. 21, 2006

(54) WELDING SHIELD

(75) Inventor: Roger L. DeYoung, Franklin, TN (US)

(73) Assignee: Campbell Hausfeld/Scott Fetzer Company, Harrison, OH (US)

( * ) Notice: Subject to any disclaimer, the term of this patent is extended or adjusted under 35 U.S.C. 154(b) by 69 days.

(21) Appl. No.: 10/865,543

(22) Filed: Jun. 10, 2004

(65) Prior Publication Data

US 2005/0273900 A1    Dec. 15, 2005

(51) Int. Cl.
*A42B 1/00* (2006.01)
(52) U.S. Cl. .................................. 2/8; 2/9; 2/11; 2/429
(58) Field of Classification Search ...................... 2/6.3, 2/6.5, 6.7, 427, 424, 429, 439, 433, 8, 9, 2/441, 432, 443, 11; 219/147; 351/47, 86; 359/811, 819, 892; 49/463, 466, 316; 52/204.597, 52/204.71
See application file for complete search history.

(56) References Cited

U.S. PATENT DOCUMENTS

| | | | | |
|---|---|---|---|---|
| 1,378,255 A | * | 5/1921 | Malcom | .............................. 2/8 |
| 1,723,308 A | * | 8/1929 | Sipe | ....................... 52/204.597 |
| 2,129,404 A | * | 9/1938 | Bugatti | .................. 52/204.597 |
| 2,505,893 A | * | 5/1950 | Haas | ............................ 52/208 |
| 2,685,641 A | * | 8/1954 | McDowell | .................. 362/375 |
| 2,736,404 A | * | 2/1956 | Clingman | ............... 52/204.597 |
| 2,755,728 A | * | 7/1956 | Frisby | ......................... 454/275 |
| 3,025,390 A | * | 3/1962 | Woodcock | ................... 362/362 |
| 3,078,119 A | * | 2/1963 | Premo et al. | ................. 52/208 |
| 3,135,963 A | * | 6/1964 | Gongoll | .............................. 2/9 |
| 3,347,134 A | * | 10/1967 | Nerwin | ......................... 353/120 |
| 3,533,686 A | * | 10/1970 | O'Shea | .......................... 351/61 |
| 3,577,563 A | * | 5/1971 | Raschke | ............................. 2/8 |
| 4,097,929 A | * | 7/1978 | Lowe et al. | ...................... 2/10 |
| 4,196,982 A | * | 4/1980 | Watkins | ......................... 351/86 |
| 4,724,550 A | * | 2/1988 | Fox et al. | ....................... 2/428 |
| 4,748,695 A | * | 6/1988 | Shigematsu et al. | ............ 2/424 |
| 5,062,156 A | * | 11/1991 | Siegal | ................................ 2/8 |
| 5,809,707 A | * | 9/1998 | Bargados et al. | ......... 52/204.62 |
| 6,210,001 B1 | * | 4/2001 | Huang | .......................... 351/86 |
| 2004/0210976 A1 | * | 10/2004 | Huh | .................................. 2/8 |

OTHER PUBLICATIONS

Campbell Hausfeld "Operating Instructions and Parts Manual" for "Shielded Metal Arc Welder", pp. 1-4, Apr. 1997.

* cited by examiner

*Primary Examiner*—Rodney M. Lindsey
(74) *Attorney, Agent, or Firm*—Jones Day (57) ABSTRACT

An apparatus includes a wall defining an opening. A first bracket is connected to the wall and defines a first channel. A second bracket is located across the wall opening from the first bracket and defines a second channel. A hinge connects the second bracket to the wall such that the second bracket can pivot from a first position in which the second channel is open toward the wall opening to a second position in which the second channel is open toward the first channel. The brackets are configured to retain the lens in an installed position in which the lens extends across the wall opening, the first bracket captures a first end of the lens, the second bracket is in its second position, and the second channel captures a second end of the lens.

35 Claims, 6 Drawing Sheets

WELDING SHIELD

TECHNICAL FIELD

This application relates to welding shields.

BACKGROUND

During the process of welding, an intensely bright light and a shower of sparks is emitted from a part being welded. The welder's eyes can be shielded from the light and sparks by a welding shield. The welding shield includes a shield plate, with a dark tinted glass window, and a handle. Grasping the handle, the welder holds the shield plate up in front of his face while welding. This enables the welder to view the part being welded through the tinted glass while shielding his eyes from the light and sparks.

SUMMARY

An apparatus comprises a wall defining an opening. A first bracket is connected to the wall and defines a first channel. A second bracket is located across the wall opening from the first bracket and defines a second channel. A hinge connects the second bracket to the wall such that the second bracket can pivot from a first position in which the second channel is open toward the wall opening to a second position in which the second channel is open toward the first channel. The brackets are configured to retain the lens in an installed position in which the lens extends across the opening, the first bracket captures a first end of the lens, the second bracket is in its second position, and the second channel captures a second end of the lens.

Preferably, another hinge connects the first bracket to the wall such that the first bracket can pivot from a first position in which the first channel is open toward the wall opening to a second position in which the first channel is open toward the second channel. When the second bracket is in the second position, the hinge resiliently urges the second bracket back toward the first position. The second bracket has an engagement surface extending from the second channel opening in a direction away from the hinge, configured to be pushed by a finger to pivot the second bracket from the first position to the second position.

Also, preferably, the brackets enable the lens to be brought into the installed position by inserting the first end of the lens into the first channel and then pivoting the second end of the lens about the first channel toward and into the second channel. The second bracket has a smooth engagement surface extending from the second channel in a direction away from the hinge. The engagement surface is configured for the lens, while pivoting toward the second channel, to slide along the engagement surface toward the second channel with the engagement surface resiliently pressing the lens into the first channel. The sliding of the lens against the engagement surface toward the second channel increasingly flexes the engagement surface upward for the engagement surface to ride up and over the lens. The wall, the brackets and the hinge are molded as a one-piece structure. The apparatus is included as part of a welding shield.

DESCRIPTION

Figure 1:
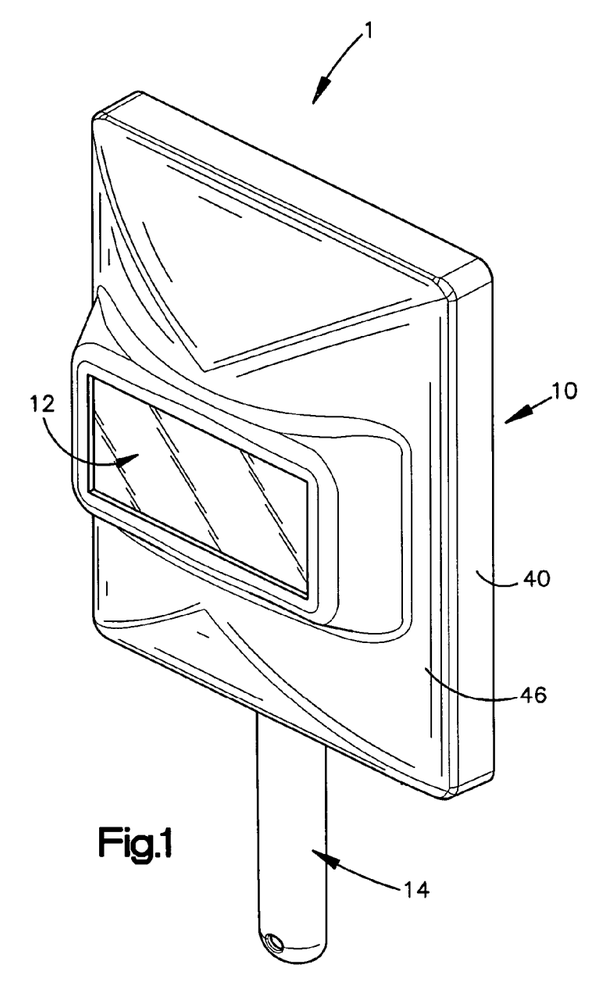
FIG. 1 is a perspective view of a welding shield, including a lens mounted in a shield plate.

The apparatus 1 shown in FIG. 1 has parts that are examples of the elements recited in the claims.

The apparatus 1 is a handheld welding shield. It is used to shield a welder's eyes from sparks and intense light emitted from a part being welded. The shield 10 includes a shield plate 10, a tinted lens 12 installed in the shield plate 10, and a handle 14. Grasping the handle 14, the welder holds the shield plate 12 up in front of his face while welding. This enables the welder to view the part being welded through the lens 12 while shielding his eyes from the light and sparks.

Figure 2:
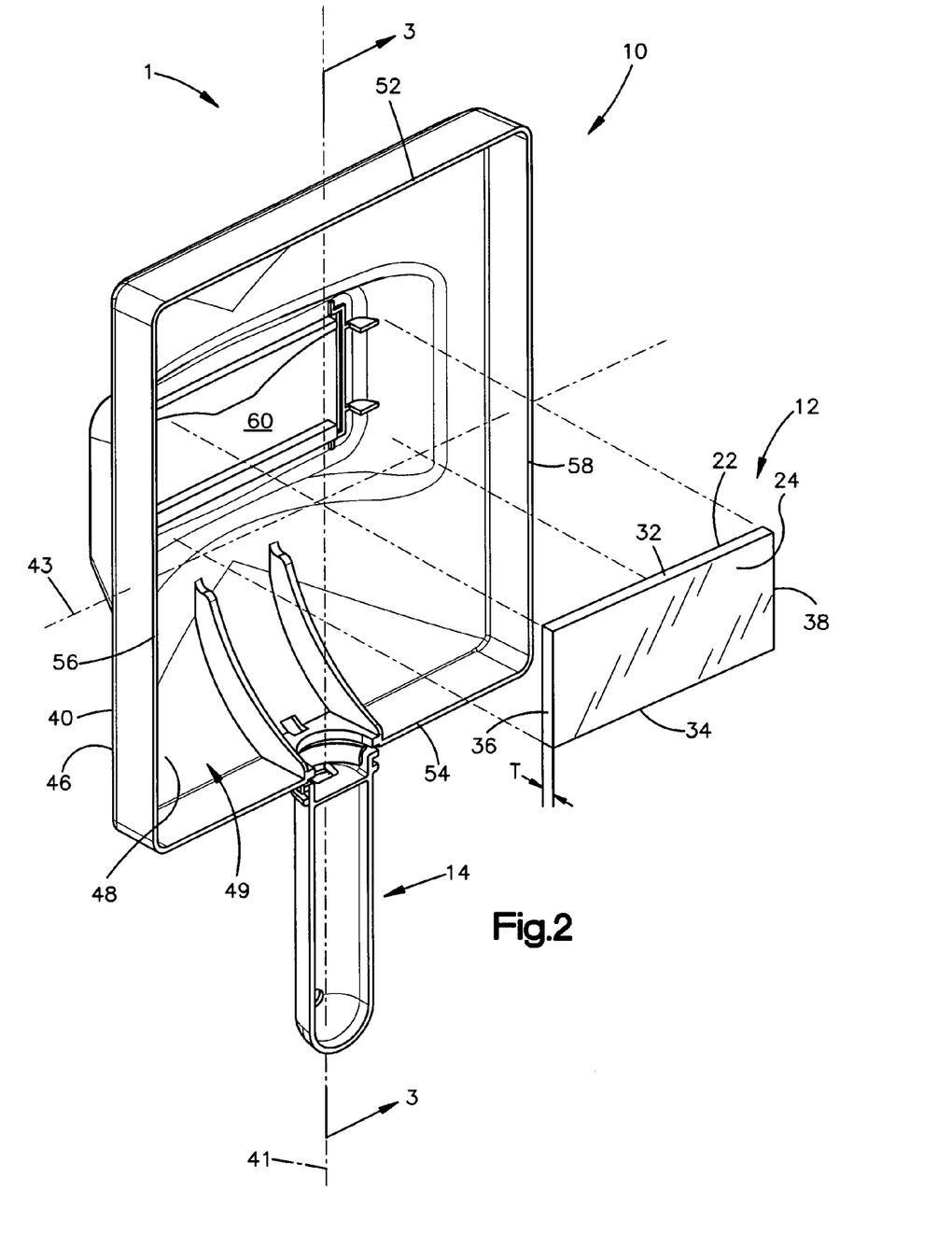
FIG. 2 is another perspective view of the shield, with the lens separated from the shield plate.

FIG. 2 is an exploded view of the shield plate 10 and the lens 12. The lens 12 is a piece of transparent material, preferably glass, that is darkly tinted to let only a portion of the light through. It has front and rear surfaces 22 and 24. It further has a rectangular periphery defined by a top and bottom ends 32 and 34 and two opposite sides 36 and 38.

Figure 3:
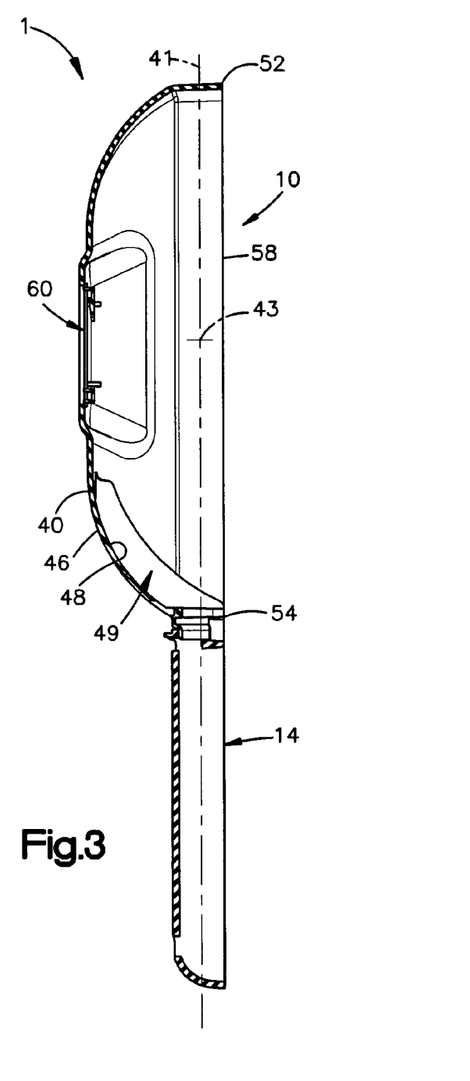
FIG. 3 is a sectional side view taken at line 3—3 of FIG. 2.

As shown in FIGS. 2 and 3, the shield plate 10 is centered on perpendicular longitudinal and lateral axes 41 and 43. The plate 10 includes a wall 40 with front and rear surfaces 46 and 48. The wall 40 is pan-shaped, with the rear surface 48 defining a shield cavity 49. The wall 40 has a rectangular periphery defined by laterally extending top and bottom edges 52 and 54 and two opposite longitudinally extending side edges 56 and 58. The handle 14 projects longitudinally downward from the bottom edge 54 and is laterally centered between the side edges 56 and 58

Figure 4:
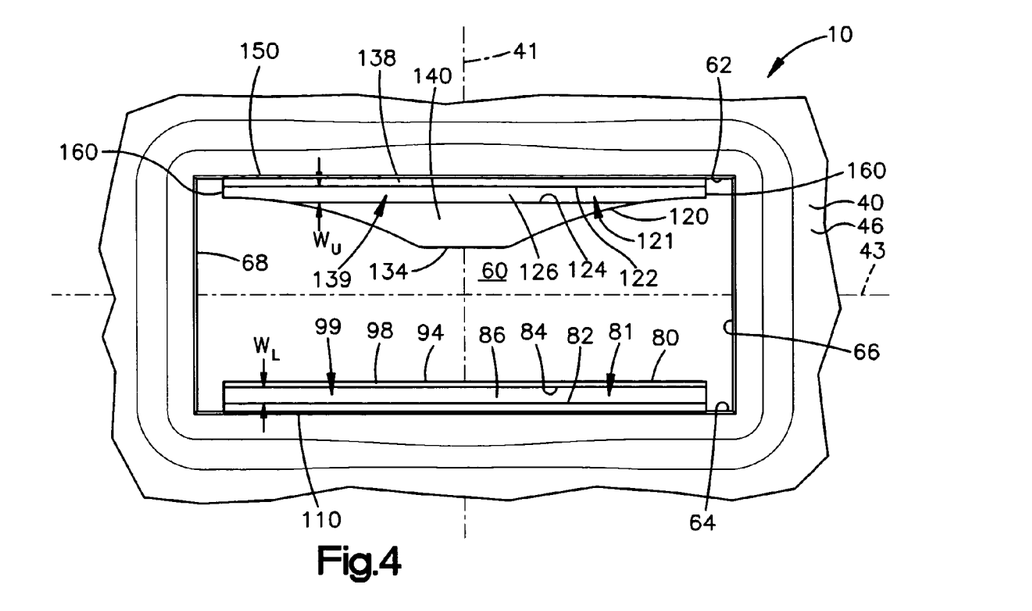
FIG. 4 is an expanded front view of a section of FIG. 3.
Figure 5:
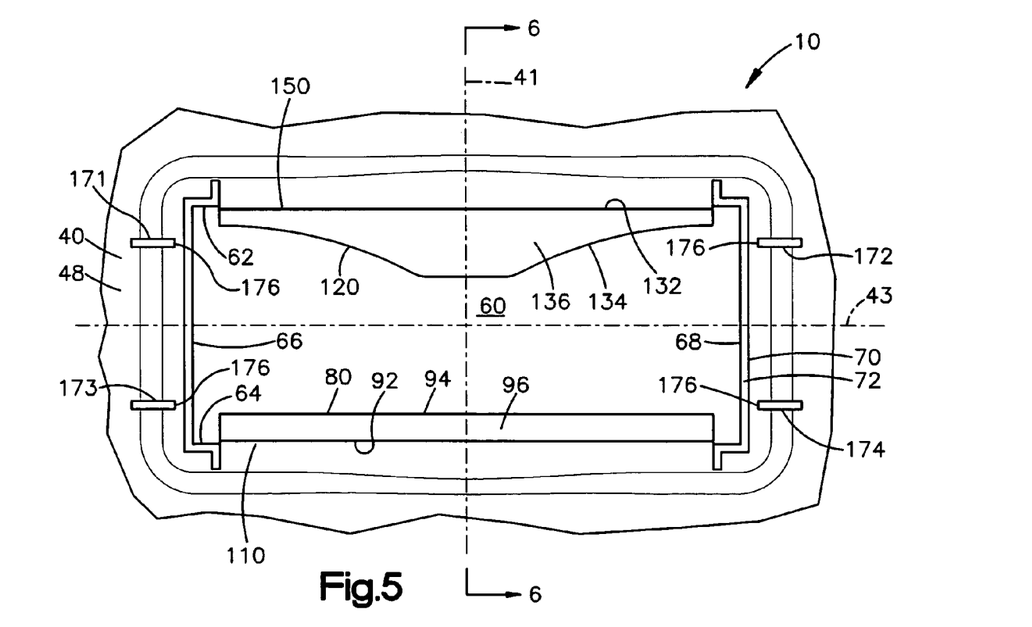
FIG. 5 is an expanded rear view of the section of FIG. 3.

As shown in FIGS. 4 and 5, the wall 40 has a rectangular opening 60 defined by top and bottom edges 62 and 64 of the wall 40 and two opposing side edges 66 and 68 of the wall 40.

As shown in FIG. 5, the opening 60 is bracketed by a lip 70 that projects rearwardly from the rear surface 48 of the wall 40. The lip 70 extends along the full lengths of the two side edges 66 and 68 and along portions of the upper and lower edges 62 and 64. The lip 70 has a generally rectangular rear edge 72 that brackets the wall opening 60 and abuts the front face 22 of the lens 12 (FIG. 2) when the lens 12 is installed on the shield plate 10.

A lower bracket 80 extends laterally along, and is adjacent to, the bottom edge 64 of the wall opening 60. The lower bracket 80 has a cross-sectional profile shown head-on in FIG. 6. This profile is uniform along the length of the bracket 80. It is characterized by a laterally extending channel 81. The channel 81 is bounded on three sides by first and second inner side surfaces 82 and 84 and an inner end surface 86 of the bracket 80. The channel 81 is configured to closely receive the bottom 34 of the lens 12 when the lens 12 is mounted on the shield plate 10. Accordingly, a width $W_L$ of the bracket cavity 81, which is the distance between the inner side surfaces 82 and 84, equals, at least approximately, a thickness T (FIG. 2) of the lens 12.

Figure 6:
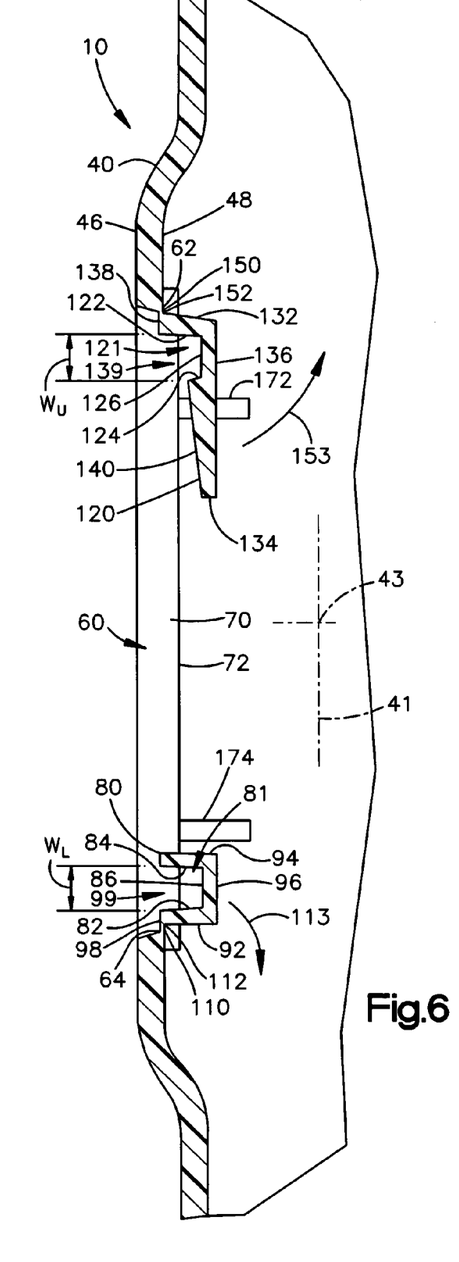
FIG. 6 is a sectional side view taken at line 6—6 of FIG. 5.

First and second outer side surfaces 92 and 94 of the bracket 80 are respectively parallel to the first and second inner side surfaces 82 and 84. First and second opposite outer end surfaces 96 and 98 extend from the first outer side surface 94 to the second outer side surface 94. An opening 99 in the second outer end surface 98 provides access to the cavity 81.

The lower bracket 80 and the bottom edge 64 of the wall opening 60 are connected together along their lengths by a hinge 110. The hinge 110 extends laterally along an edge 112 of the bracket 80 where the first outer side surface 92 and the second outer end surface 98 meet. In this example, the hinge 10 is a living hinge, molded as a one-piece structure with the wall 40 and the lower bracket 80. It bridges the bracket 80 and the shield wall 40 and is sufficiently thin and flexible to function as a hinge between them. As indicated by arrow 113, the hinge 110 enables the lower bracket 80 to be pivoted away from its initial as-molded position shown in FIG. 6. Concurrently, the hinge 110 resiliently urges the lower bracket 80 back toward its initial as-molded position. The bracket 80 is flexible, but not as flexible as the living hinge 110.

An upper bracket 120 extends laterally along, and is adjacent to, the top edge 62 of the wall opening 60. The upper bracket 120 has a cross-sectional profile shown head-on in FIG. 6. As with the lower bracket 80, the profile of the upper bracket 120 is characterized by a laterally extending channel 121. The channel 121 is bounded on three sides by first and second opposite inner side surfaces 122 and 124 and an inner end surface 126 of the bracket 120. The upper channel 121 is configured to closely receive the top 32 of the lens 12 (FIG. 2) when the lens 12 is installed on the shield plate 10. Accordingly, a width $W_U$ of the upper channel 121, which is the distance between the inner side surfaces 122 and 124, equals, at least approximately, the thickness T (FIG. 2) of the lens 12.

The upper bracket 120 further has first and second outer side surfaces 132 and 134. A first outer end surface 136 extends from the first outer side surface 132 to the second outer side surface 134. A second outer end surface 138 extends from the first outer side surface 132 to a front opening 139 of the channel 120. A third outer end surface 140 extends from the front opening 139, in a direction away from the first outer side surface 132, to the second outer side surface 134.

The upper bracket 120 and the upper edge 62 of the wall opening 60 are connected together along their lengths by a hinge 150. The hinge 150 extends laterally along an edge 152 of the bracket 120 where the first outer side surface 132 and the second outer end surface 138 meet. In this example, the hinge 150 is a living hinge molded as a one-piece structure with the wall 40 and the upper bracket 120. It bridges the wall 40 and the upper bracket 120 and is sufficiently thin and flexible to function as a hinge between them. As indicated by arrow 153, the hinge 150 enables the upper bracket 120 to be pivoted away from its initial as-molded position shown in FIG. 6. Concurrently, the hinge 150 resiliently urges the upper bracket 120 back toward its initial position. The upper bracket 120 is flexible, but not as flexible as the living hinge 150.

The profile of the upper bracket 120 is not uniform along its length. As shown in FIG. 4, the second outer side surface 134 recedes toward the upper edge 62 with increasing proximity to the laterally opposite sides 160 of the upper bracket 120. In fact, at the laterally opposite sides 160, the entire second inner side surface 124 and a portion of the inner end surface 126 are absent.

As shown in FIG. 5, first and second upper retaining bosses 171 and 172 and first and second lower retaining bosses 173 and 174 extend rearwardly from the rear surface 48 of the wall 40. The first bosses 171 and 173 are adjacent to the first edge 66 of the opening 60. The second bosses 172 and 174 are adjacent to the second edge 68 of the opening 60. Each boss 171, 172, 173 and 174 has an abutment surface 176 facing laterally inward. The abutment surfaces 176 are configured to abut the sides 36 and 38 (FIG. 2) of the lens 12 when the lens 12 is in the installed position.

The shield plate 10 can be injection molded. The molding process entails 1) injecting heat-softened plastic resin between front and rear core faces of a mold (not shown), 2) waiting for the plastic to harden, 3) retracting the front and rear cores away from the shield plate, and 4) ejecting the shield plate from the mold.

The as-molded configuration of the shield plate 40 is shown in FIG. 6. In this configuration, the channels 80 and 120 are open toward the wall opening 60 in that the channel openings 99 and 139 face forward toward the wall opening 60. This enables the front core of the mold to form the channels 81 and 121 along with features of the front surface 46. After the plastic hardens, the front core can be withdrawn from the bracket channels 81 and 121 when being retracted from the front surface 46. Accordingly, formation of the upper and lower channels 81 and 121 does not require additional cores, which would be the case if the channels 81 and 121 were open in a longitudinal or lateral direction.

Figure 7:
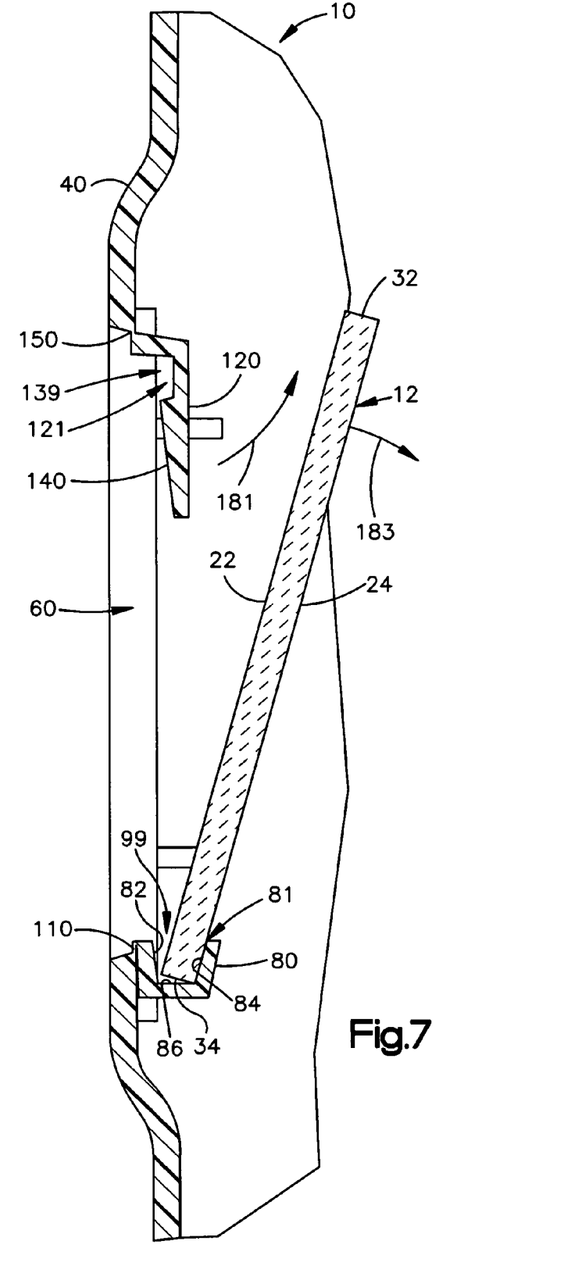
FIGS. 7–10 are sectional side views similar to FIG. 6, showing the lens and the plate in sequential steps for installing the lens onto the plate.

The lens 12 (FIG. 2) can be installed in the shield plate 12 as follows. First, as indicated by arrow 113, the lower bracket 80 is pivoted about its hinge 110 rearward and downward from its initial, as-molded, position. This continues until the bracket 80 reaches a second position in which the lower channel 80 is open toward the upper channel 121, i.e., the lower channel opening 99 faces the upper channel 121, as shown in FIG. 7. Then the lens 12 is inserted into the lower channel 81.

Figure 8:
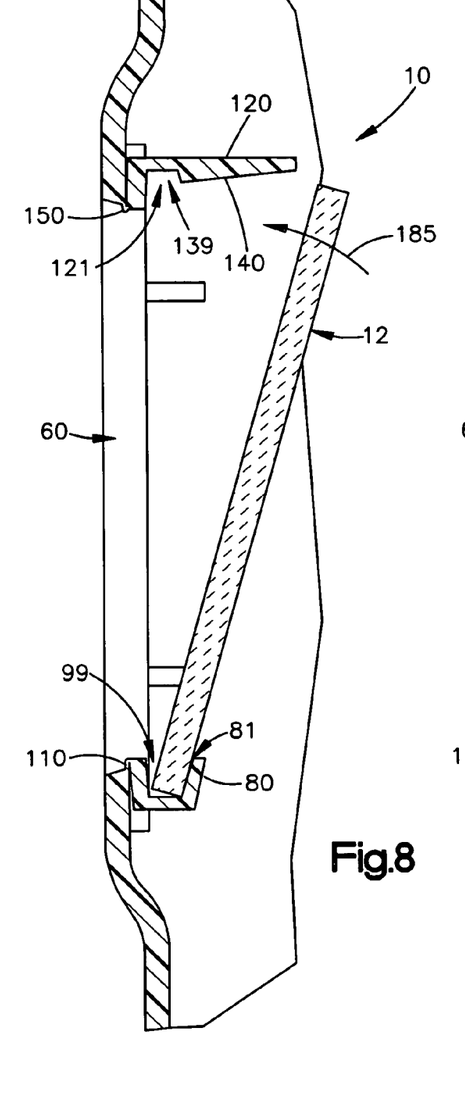

Next, the third outer end surface 140 is pushed rearward by a finger. As indicated by arrow 181, this pivots the upper bracket 120 rearward about its living hinge 150 rearward and upward from its initial as-molded position. This continues until the bracket 120 reaches a second position in which the upper channel opening 139 faces the opposite channel 81, as shown in FIG. 8, and the third outer end surface 140 is above the lens 12. Concurrently, as indicated by arrow 183 in FIG. 7, the lens 12 is tilted rearward about the lower channel 81. This continues until the third outer end surface 140 is above the lens 12, as shown in FIG. 8. The tilting motions indicated by arrows 181 and 183 in FIG. 7 are enabled, but resisted, by the flexibility of the brackets and hinges 80, 120, 110 and 150.

Figure 9:
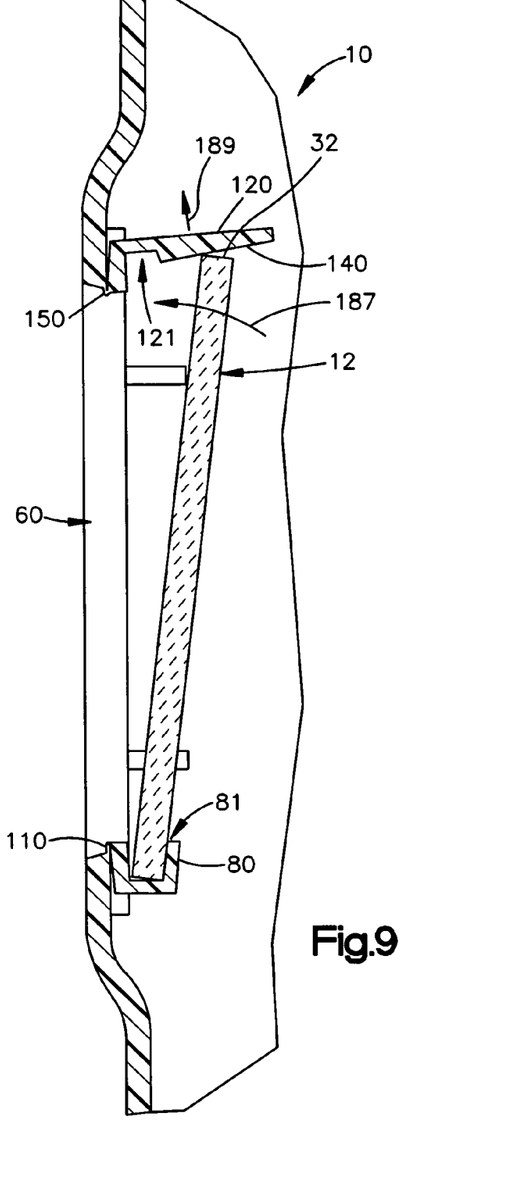

Next, as indicated by the arrow 185 in FIG. 8, the lens 12 is pivoted forward toward the wall opening 60. While pivoting increasingly forward, as indicated by arrow 187 in FIG. 9, the top 32 of the lens 12 slides against the third outer end surface 140 of the bracket 120. In doing so, the lens 12 pushes the third outer end surface 140 increasingly higher as indicated by arrow 189. Concurrently, the third outer end surface 140 resiliently bears down against the lens 12, thus pressing it into the first channel 81.

As the lens 12 continues forward (arrow 187), the third outer end surface 140 rides up (arrow 189) and over the lens 12. The lens 12 thus finally snaps into its installed position, shown in FIG. 10.

Figure 11:
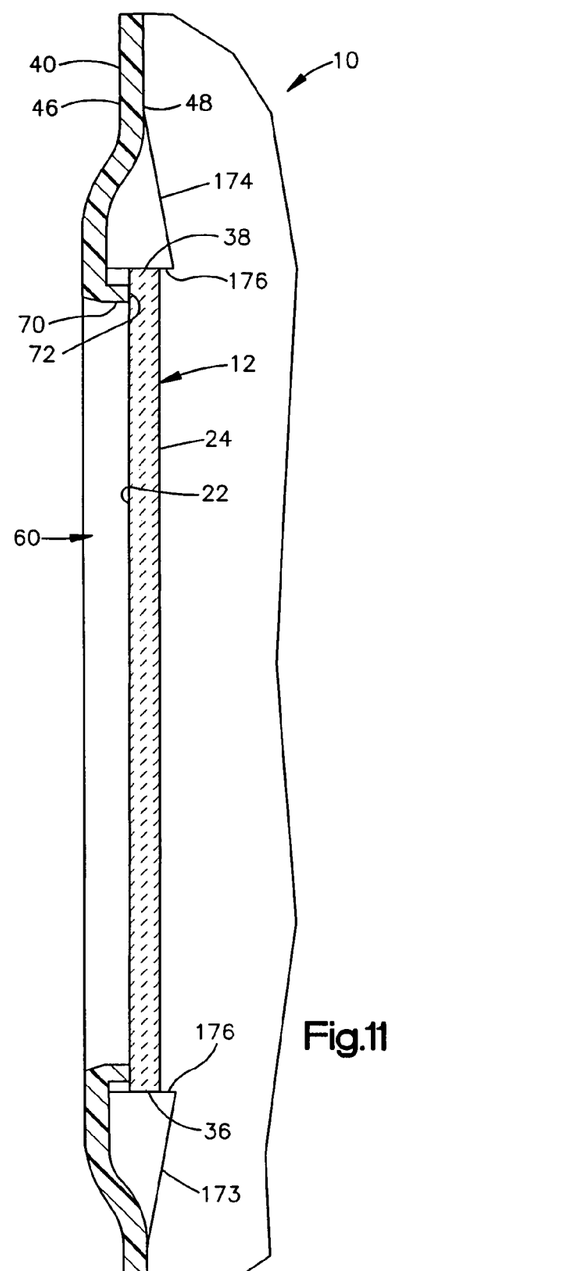
FIG. 11 is a sectional top view taken at line 11—11 of FIG. 10.

The installed position is characterized by the following features: The first outer surfaces 92 and 132 of both brackets 80 and 120 abut the rear surface 48 of the wall 40. The channel openings 99 and 139 face each other. A field of view is bounded longitudinally by the hinges 110 and 150 (FIG. 5). The brackets 80 and 120, including the second inner side surfaces 82 and 122 of the brackets 80 and 120, do not cross into the field of view. The bracket channels 81 and 121 capture the lens 12. Forward movement of the lens 12 is prevented by abutment of the front surface 22 of the lens 12 against both the rear edge 72 of the lip 70 and the first inner surfaces 82 and 122 of the brackets 80 and 120. Rearward movement of the lens 10 is prevented by abutment of the rear surface 24 of the lens 12 against the second inner surfaces 84 and 124 of the brackets 80 and 120. As shown in FIGS. 11, lateral movement of the lens 12 is limited, and prevented, by abutment of the sides 36 and 38 of the lens 12 against the abutment surfaces 176 of the retaining bosses 171, 172, 173 and 174 (FIG. 5).

Figure 10:
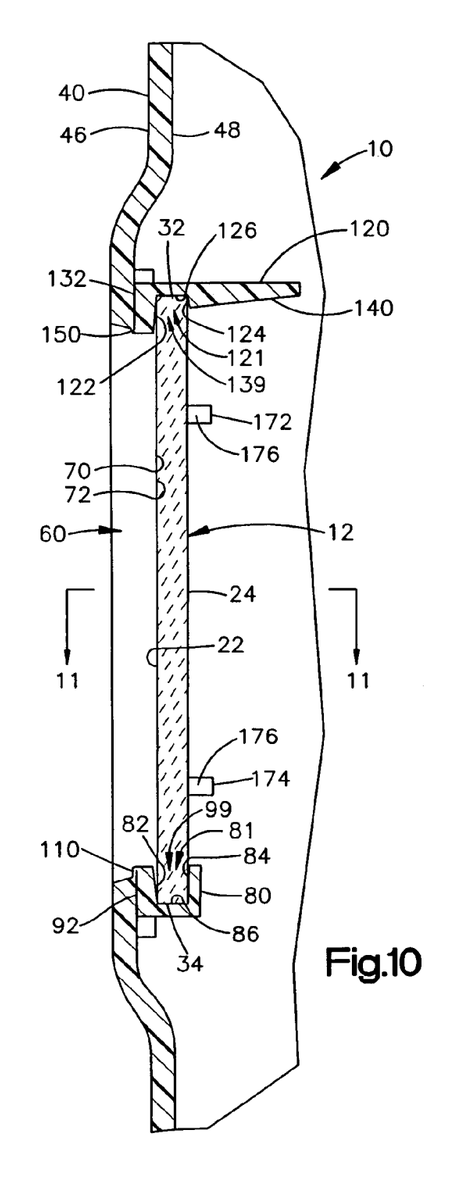

As is apparent in FIG. 10, the lens 12 can be removed from the shield plate 40 by pushing up on the third outer end surface 140 of the upper bracket 120 to release the lens 12. The lens 12 can then be tilted rearward and lifted out of the lower bracket 80.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have elements that do not differ from the literal language of the claims, or if they include equivalent structural elements with insubstantial differences from the literal language of the claims.

The invention claimed is:

1. An apparatus comprising:
   a wall defining an opening;
   a first bracket connected to the wall and defining a first channel;
   a second bracket located across the wall opening from the first bracket and defining a second channel; and
   a hinge connecting the second bracket to the wall such that the second bracket can pivot from a first position in which the second channel is open toward the wall opening to a second position in which the second channel is open toward the first channel;
   the brackets being configured to retain a lens in a removably installed position in which the lens extends across the wall opening, the first channel captures a first end of the lens, the second bracket is in its second position, and the second channel captures a second end of the lens.

2. The apparatus of claim 1 further comprising another hinge connecting the first bracket to the wall such that the first bracket can pivot from a first position in which the first channel is open toward the wall opening to a second position in which the first channel is open toward the second channel.

3. The apparatus of claim 1 wherein, when the second bracket is in the second position, the hinge resiliently urges the second bracket back toward the first position.

4. The apparatus of claim 1 wherein the second bracket has an engagement surface extending from the second channel in a direction away from the hinge, configured to be pushed by a finger to pivot the second bracket from the first position to the second position.

5. The apparatus of claim 1 wherein the brackets enable the lens to be brought into the installed position by inserting the first end of the lens into the first channel and then pivoting the second end of the lens about the first channel toward and into the second channel.

6. The apparatus of claim 5 wherein the second bracket has a smooth engagement surface extending from the second channel in a direction away from the hinge, and is configured for the lens, while pivoting toward the second channel, to slide along the engagement surface toward the second channel with the engagement surface resiliently pressing the lens into the first channel.

7. The apparatus of claim 6 wherein the sliding of the lens against the engagement surface toward the second channel increasingly flexes the engagement surface upward for the engagement surface to ride up and over the lens.

8. The apparatus of claim 1 wherein the second bracket is elongated and is connected along its length by the hinge to the wall.

9. The apparatus of claim 1 wherein die wall opening is rectangular with first and second opposite end edges and first and second opposite side edges, with the first bracket extending along the first end edge and the second bracket extending along the second end edge.

10. The apparatus of claim 1 wherein die wall, the brackets and the hinge are molded as a one-piece structure.

11. The apparatus of claim 1 wherein a surface of the second bracket engages the wall when the lens is in the installed position.

12. The apparatus of claim 1 further comprising a lens configured to be installed in the apparatus in the installed position.

13. A welding shield including the apparatus of claim 1.

14. An apparatus comprising:
   a wall defining an opening;
   a first bracket defining a first channel;
   a first hinge connecting the first bracket to the wall;
   a second bracket located across the wall opening from the first bracket and defining a second channel; and
   a second hinge connecting the second bracket to the wall;
   the brackets being configured to retain a lens in a removably installed position in which the lens extends across the wall opening, the first bracket captures a first end of the lens, and the second bracket captures a second end of the lens.

15. The apparatus of claim 14 wherein the second hinge enables the second bracket to pivot from a first position in which the second channel is open toward the wall opening to a second position in which the second channel is open toward the first channel while resiliently urging the second bracket back toward the first position.

16. The apparatus of claim 15 wherein the second hinge has an engagement surface extending from the second channel in a direction away from the hinge configured to be pushed by a finger to pivot the second bracket from the first position to the second position.

17. The apparatus of claim 14 wherein the brackets enable the lens to be brought into the installed position by inserting the first end of the lens into the first channel and then pivoting the second end of the lens about the first channel toward and into the second channel.

18. The apparatus of claim 17 wherein the second bracket has a smooth engagement surface extending from the second channel in a direction away from the hinge, and is configured for the lens, while pivoting toward the second channel, to slide along the engagement surface toward the second channel as the engagement surface resiliently presses the lens into the first channel.

19. The apparatus of claim 18 wherein the sliding of the lens against the engagement surface toward the second channel increasingly flexes the engagement surface upward for the engagement surface to ride up and over the lens.

20. The apparatus of claim 14 wherein the second bracket is elongated and is connected along its length by the second hinge to the wall.

21. The apparatus of claim 14 wherein the wall opening is rectangular with first and second opposite end edges and first and second opposite side edges, and the first bracket extends along the first end edge and the second bracket extends along the second end edge.

22. The apparatus of claim 14 wherein the wall, the brackets and the hinges are molded as a one-piece structure.

23. The apparatus of claim 14 wherein a surface of the second bracket engages the wall when the lens is in the installed position.

24. The apparatus of claim 14 further comprising a lens configured to be installed in the apparatus in the installed position.

25. A welding shield including the apparatus of claim 14.

26. An apparatus comprising:
a wall defining an opening;
a first bracket connected to the wall and defining a first channel; and
a second bracket located across the wall opening from the first bracket, defining a second channel and flexibly connected to the wall by a hinge that enables the second bracket to pivot from a first position in which the second channel is open toward the wall opening to a second position in which the second channel is open toward the first channel;
the brackets being configured for a lens to be brought into a removably installed position by inserting the lens into the first channel, and then pivoting the lens about the first channel toward and into the second channel for the lens to extend across the wall opening.

27. An apparatus comprising:
a wall having an opening defined by two opposite end edges of the wall and two opposite side edges of the wall;
two brackets, each flexibly connected to the wall adjacent a respective end edge by a hinge and defining a channel;
two abutment structures, each extending from the wall adjacent a respective side edge; and
a lens having two opposite ends and two opposite sides, being mountable in a removably installed position in which the ends of the lens are captured in respective brackets, and lateral movement of the lens is limited by abutment of the sides against respective abutment structures.

28. The apparatus of claim 27 wherein the opposite ends of the lens extend beyond the opening into the respective brackets.

29. An apparatus comprising:
a wall defining an opening;
a first bracket connected to the wall and defining a first channel; and
a second bracket located across the wall opening from the first bracket, defining a second channel and flexibly connected to the wall;
the brackets being configured to retain a lens in a removably installed position in which the lens extends across the opening with one end of the lens extending beyond the opening into the first channel and an opposite end of the lens extending beyond the opening into the second channel.

30. The apparatus of claim 29 wherein also the first bracket is flexibly connected to the wall.

31. The apparatus of claim 29 wherein the brackets enable the lens to be brought into the installed position by inserting the lens into the first channel and then pivoting the lens about the first channel toward the second channel while a surface of the second bracket slides up and over the lens to bring the lens into the second channel.

32. An apparatus comprising:
a wall defining an opening;
a first bracket connected to the wall and defining a first channel; and
a second bracket located across the opening from the first bracket, defining a second channel, and flexibly connected to the wall to be pivotable from a first position in which the second channel is open toward the opening to a second position in which the second channel is open toward the first channel;
the brackets being configured to retain a lens in a removably installed position in which the lens extends across the wall opening and is captured in the first and second channels.

33. The apparatus of claim 32 wherein the second bracket is resiliently urged toward the first position.

34. The apparatus of claim 32 wherein also the first bracket is flexibly connected to the wall to he pivotable from a first position in which the first channel is open toward the wall opening to a second position in which the first channel is open toward the second channel.

35. The apparatus of claim 32 wherein the brackets enable the lens to be brought into the installed position by inserting the lens into the first channel and ten pivoting the lens about the first channel toward the second channel while a surface of the second bracket slides up and over the lens to bring the lens into the second channel.

* * * * *

UNITED STATES PATENT AND TRADEMARK OFFICE
CERTIFICATE OF CORRECTION

PATENT NO. : 7,000,251 B2
DATED : February 21, 2006
INVENTOR(S) : DeYoung

It is certified that error appears in the above-identified patent and that said Letters Patent is hereby corrected as shown below:

Column 6,
Lines 15 and 20, "die" should read -- the --.

Column 8,
Line 40, "he" should read -- be --.
Line 46, "ten" should read -- then --.

Signed and Sealed this

Twenty-fifth Day of April, 2006

JON W. DUDAS
*Director of the United States Patent and Trademark Office*